US012768812B2

(12) United States Patent
Li et al.

(10) Patent No.: US 12,768,812 B2
(45) Date of Patent: Oct. 20, 2026

(54) CAPILLARY ELECTROPHORESIS PURITY ANALYSIS OF COMPLEMENTARY STRAND NUCLEIC ACID MOLECULES

(71) Applicant: DH TECHNOLOGIES DEVELOPMENT PTE. LTD., Singapore (SG)

(72) Inventors: Tingting Li, Redwood City, CA (US); Handy Yowanto, Walnut, CA (US); Elliott Jones, Redwood City, CA (US); Sahana Mollah, Redwood City, CA (US)

(73) Assignee: DH TECHNOLOGIES DEVELOPMENT PTE. LTD., Singapore (SG)

( * ) Notice: Subject to any disclaimer, the term of this patent is extended or adjusted under 35 U.S.C. 154(b) by 163 days.

(21) Appl. No.: 18/714,761

(22) PCT Filed: Dec. 16, 2022

(86) PCT No.: PCT/IB2022/062337

§ 371 (c)(1),
(2) Date: May 30, 2024

(87) PCT Pub. No.: WO2023/111966

PCT Pub. Date: Jun. 22, 2023

(65) Prior Publication Data

US 2024/0418674 A1 Dec. 19, 2024

Related U.S. Application Data

(60) Provisional application No. 63/290,822, filed on Dec. 17, 2021.

(51) Int. Cl.
*G01N 27/447* (2006.01)
*C12N 15/01* (2006.01)
(Continued)

(52) U.S. Cl.
CPC ....... *G01N 27/44726* (2013.01); *C12N 15/01* (2013.01); *C12Q 1/6806* (2013.01); *G01N 27/44747* (2013.01); *G01N 27/44791* (2013.01)

(58) Field of Classification Search
CPC ....... G01N 27/44726; G01N 27/44747; G01N 27/44791; C12Q 1/6806; C12N 15/101
See application file for complete search history.

(56) References Cited

U.S. PATENT DOCUMENTS 5,874,213 A 2/1999 Cummins et al.

FOREIGN PATENT DOCUMENTS

WO 2000/028314 5/2000
WO 2012/106244 8/2012

OTHER PUBLICATIONS

Luo et al., "RNA Analysis for CRISPR by capillary electrophoresis with laser-induced fluorescence detection," Drug Discovery and Development, SCIEX Separations, 2019 (Year: 2019).*

(Continued)

*Primary Examiner* — Alexander S Noguerola
(74) *Attorney, Agent, or Firm* — Lathrop GPM LLP; Malaika O.D. Tyson; Jason Kuchar

(57) ABSTRACT

The presently described and claimed disclosure relates to method for characterizing nucleic acid purity comprising denaturing a nucleic acid sample, loading the nucleic acid sample onto a capillary electrophoresis (CE) capillary, wherein the CE capillary is filled with a buffer comprising a polymer matrix, applying a separation voltage to the CE capillary, wherein during the separation of the nucleic acids, the temperature of the CE capillary is increased, and detecting nucleic acids separated from the nucleic acid sample with a detector. Kits and instructions for use are also described.

18 Claims, 18 Drawing Sheets

(51) Int. Cl.
*C12N 15/10* (2006.01)
*C12Q 1/6806* (2018.01)

(56) References Cited

OTHER PUBLICATIONS

Morris et al., "Automated design of CRISPR prime editors for 56,000 human pathogenic variants," iScience 24, 103380 Nov. 19, 2021 (Year: 2021).*
Skeidsvoll et al., "Analysis of RNA by capillary electrophoresis,", Electrophoresis 1996, 17, 1512-1517 (Year: 1996).*
Nina Petersson, Thesis—"Optimisation of capillary gel electrophoresis method for enhanced separation of mRNA shortmers," Uppsala Universitet, Feb. 2018 (Year: 2018).*
Wang et al.,"Characterization of denaturation and renaturation of DNA for DNA hybridization," Environmental Health and Toxicology, vol. 29, Article ID: e2014007, 8 pages, 2014 (Year: 2014).*
Ghoshal B, Vong B, Picard CL, Feng S, Tam JM, Jacobsen SE (2020) A viral guide RNA delivery system for CRISPR-based transcriptional activation and heritable targeted DNA demethylation in Arabidopsis thaliana. PLoS Genet 16(12): e1008983 (Year: 2020).*
Valenti et al., "Characterization of Oligonucleotide-Derived Conjugates by Capillary Electrophoresis: Method Development and Qualification," eurofilms—Lancaster Laboratories, publication date unknown. (Year: 2025).*
Sumitomo et al., "RNA Separation by In-Capillary Denaturing Gel Electrophoresis Using Carboxylic Acid Denaturants," Biophysical Chemistry 2008; 52: 133 (Year: 2008).*
Google machine translation of Sumitomo et al., "RNA Separation by In-Capillary Denaturing Gel Electrophoresis Using Carboxylic Acid Denaturants," Biophysical Chemistry 2008; 52: 133 (Year: 2008).*
PCT, International Preliminary Report on Patentability, regarding to PCT Application No. PCT/IB2022/062337, 11 pages, mailed Jun. 27, 2024.
International Search Report and Written Opinion corresponding to International Patent Application No. PCT/IB2022/062337, mailed Mar. 21, 2023.
Li Tingting et al., "Development of purity analysis methods for synthetic prime editing guide RNAs (pegRNAs) with high-level secondary structures for prime editing research applications", Dec. 1, 2022 (Dec. 1, 2022), Retrieved from the Internet: URL:https://sciex.com/tech-notes/biopharma/development-of-purity-analysis-methods-for-synthetic-prime-editi, XP093030838.
Karger B L et al., "Capillary Electrophoresis of Proteins and Nucleic Acids", Jun. 1, 1995 (Jun. 1, 1995), vol. {0} 24, No. {0} 1, p. 579-610, Retrieved from the Internet: URL:https://www.annualreviews.org/doi/pdf/10.1146/annurev.bb.24.060195.003051, XP093030525.
Rosenblum B B et al., "Improved Single-Strand Dna Sizing Accuracy in Capillary Electrophoresis", Nucleic Acids Research, Oxford University Press, GB, vol. {0} 25, No. {0} 19, Jan. 1, 1997 (Jan. 1, 1997), p. 3925-3929, XP000891510.
Xiaofang Wang et al, "Characterization of denaturation and renaturation of DNA for DNA hybridization", Environmental Health and Toxicology, vol. {0} 29, Sep. 11, 2014 (Sep. 11, 2014), p. e2014007, XP055748014.
Sumitomo Keiko et al., "RNA separation by in-capillary denaturing polymer electrophoresis with 1,2,5-thiadiazole as an additive", Journal of Separation Science, vol. {0} 34, No. {0} 20, Oct. 1, 2011 (Oct. 1, 2011), p. 2901-2905, XP093031122.
Beckman Coulter, "Capillary Electrophoresis Supplies, Accessories & Options Putting CE To Work", Jun. 1, 2006 (Jun. 1, 2006), p. 1-52, Retrieved from the Internet: URL:http://www.beckmancoulter.de/beckman2_media/Life+Sciences/Produkte/Instrumente/Kapillarelektrophorese/Analyse+kleiner+Moleküle/Produkte/PACE+MDQ+(DAD)/Broschüren/CE+Katalog.pdf, XP055344324.
Dedionisio L A et al., "Capillary gel electrophoresis and antisense therapeutics Analysis of DNA analogs", Journal of Chromatography A, Elsevier, Amsterdam, NL, vol. {0} 735, No. {0} 1, May 31, 1996 (May 31, 1996), p. 191-208, XP004039014.

* cited by examiner

BI (Inlet Buffer Tray)

BO (Outlet Buffer Tray)

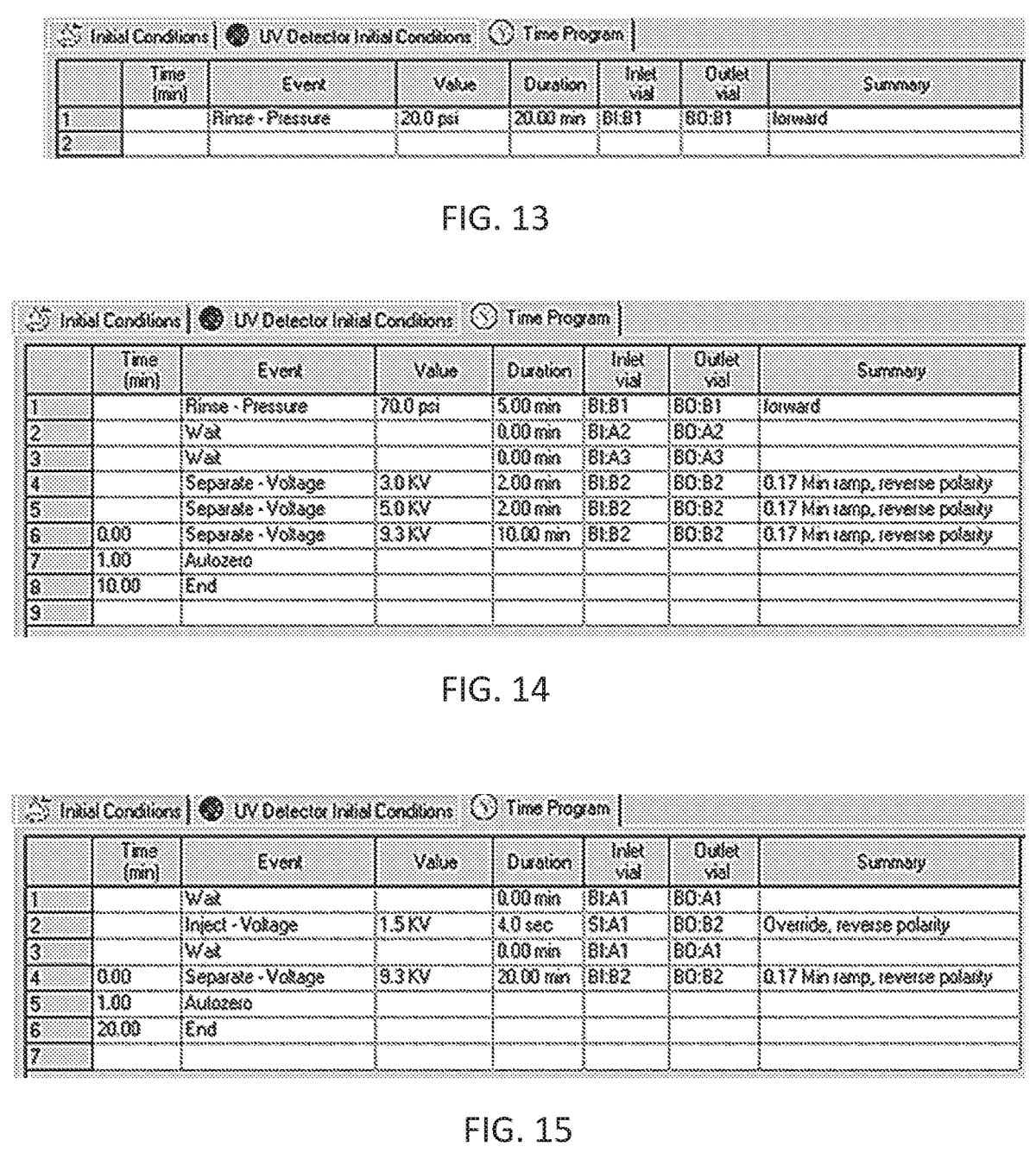

Initial Conditions | UV Detector Initial Conditions | Time Program

| | Time (min) | Event | Value | Duration | Inlet vial | Outlet vial | Summary |
|---|---|---|---|---|---|---|---|
| 1 | | Rinse - Pressure | 20.0 psi | 20.00 min | BI:B1 | BO:B1 | forward |
| 2 | | | | | | | |

FIG. 13

Initial Conditions | UV Detector Initial Conditions | Time Program

| | Time (min) | Event | Value | Duration | Inlet vial | Outlet vial | Summary |
|---|---|---|---|---|---|---|---|
| 1 | | Rinse - Pressure | 70.0 psi | 5.00 min | BI:B1 | BO:B1 | forward |
| 2 | | Wait | | 0.00 min | BI:A2 | BO:A2 | |
| 3 | | Wait | | 0.00 min | BI:A3 | BO:A3 | |
| 4 | | Separate - Voltage | 3.0 KV | 2.00 min | BI:B2 | BO:B2 | 0.17 Min ramp, reverse polarity |
| 5 | | Separate - Voltage | 5.0 KV | 2.00 min | BI:B2 | BO:B2 | 0.17 Min ramp, reverse polarity |
| 6 | 0.00 | Separate - Voltage | 9.3 KV | 10.00 min | BI:B2 | BO:B2 | 0.17 Min ramp, reverse polarity |
| 7 | 1.00 | Autozero | | | | | |
| 8 | 10.00 | End | | | | | |
| 9 | | | | | | | |

FIG. 14

Initial Conditions | UV Detector Initial Conditions | Time Program

| | Time (min) | Event | Value | Duration | Inlet vial | Outlet vial | Summary |
|---|---|---|---|---|---|---|---|
| 1 | | Wait | | 0.00 min | BI:A1 | BO:A1 | |
| 2 | | Inject - Voltage | 1.5 KV | 4.0 sec | SI:A1 | BO:B2 | Override, reverse polarity |
| 3 | | Wait | | 0.00 min | BI:A1 | BO:A1 | |
| 4 | 0.00 | Separate - Voltage | 9.3 KV | 20.00 min | BI:B2 | BO:B2 | 0.17 Min ramp, reverse polarity |
| 5 | 1.00 | Autozero | | | | | |
| 6 | 20.00 | End | | | | | |
| 7 | | | | | | | |

FIG. 15

CAPILLARY ELECTROPHORESIS PURITY ANALYSIS OF COMPLEMENTARY STRAND NUCLEIC ACID MOLECULES

RELATED APPLICATIONS

The present application is filed pursuant to 35 U.S.C. 371 as a U.S. National Phase application of International Patent Application No. PCT/IB2022/062337, which was filed Dec. 16, 2022, claim the priority benefit of U.S. Provisional Patent Application Ser. No. 63/290,822, filed Dec. 17, 2021, the content of each is hereby incorporated by reference in its entirety into this disclosure.

BACKGROUND

There are various challenges during the production of nucleic acids, including nucleic acids with complementary or partially complementary sequences. These complementary strand nucleic acid molecules tend to form more intra- or intermolecular hydrogen bonds than non-complementarity nucleic acid molecules, resulting in a distribution of high order isoforms. Manufacturers and researchers do not have rapid, easy, and reliable methods to test the purity or assess the quality of these complementary strand nucleic acid molecules as raw material or in an intermediate or final product.

With the demand for the production of complementary strand nucleic acid molecules growing, so is the need to characterize these nucleic acids better. Slab gel based electrophoresis techniques for oligonucleotides and DNA fragments analysis are semi-quantitative and cannot provide an accurate purity. Current electrophoresis workflows also have limitations for analyzing complementary strand nucleic acid molecules. The sole use of denaturants cannot entirely disrupt the hydrogen bonds of these molecules nor maintain the denatured status of the molecules during analysis, resulting in inaccurate determination of the purity assessment of the complementary strand nucleic acid molecules.

SUMMARY

The inventors have recognized the need for high precision quantification and quality control complementary strand nucleic acid molecules. The claimed and described capillary electrophoresis methods offer high resolution and provide accurate purity quantification of these complementary strand nucleic acid molecules. In some aspects, the claimed and described capillary electrophoresis methods also employ a combination of denaturing the complementary strand nucleic acid molecules and increasing the temperature of the capillary electrophoresis capillary during the separation of samples comprising these molecules. This combination disrupts the hydrogen bonds of the molecules and maintains the denatured status of the nucleic acid molecules during separation.

One aspect of the disclosure relates to a method for characterizing nucleic acid purity comprising denaturing a nucleic acid sample; loading the nucleic acid sample onto a capillary electrophoresis (CE) capillary, wherein the CE capillary is filled with a buffer comprising a polymer matrix; applying a separation voltage to the CE capillary, wherein during the separation of the nucleic acids, the temperature of the CE capillary is increased; and detecting nucleic acids separated from the nucleic acid sample with a detector.

In some aspects, the temperature of the CE capillary is increased by least about 5° C., alternatively at least about 10° C., alternatively at least about 15° C., alternatively at least about 20° C., alternatively at least about 25° C., alternatively at least about 30° C., alternatively at least about 35° C., alternatively at least about 40° C., alternatively at least about 45° C.

In an aspect, the nucleic acid sample comprises ribonucleic acid (RNA), single-stranded DNA (ssDNA), microRNA (miRNA), messenger RNA (mRNA), prime editing guide RNA (pegRNA), and/or self-complementary nucleic acids.

In an aspect, the nucleic acid sample is denatured using heat. In another aspect, the nucleic acid sample is denatured using at least one denaturing agent. In a further aspect, the denaturing agent is selected from the group consisting of helicase, acetic acid, dimethyl sulfoxide, formamide, formaldehyde, guanidine, urea, propylene glycol, sodium salicylate, 1,2,5-Thiadiazole, and combinations thereof. In yet another aspect, the nucleic acid sample is denatured using heat and sonication.

In an aspect, the nucleic acid sample is heat denatured at a temperature of about 60° C., alternatively about 65° C., alternatively about 70° C., alternatively about 75° C., alternatively about 80° C., alternatively about 85° C., alternatively about 90° C., alternatively about 95° C. In another aspect, the nucleic acid sample is heat denatured for at least about 5 minutes, alternatively at least about 10 minutes, alternatively at least about 15 minutes, alternatively at least about 20 minutes. In a further aspect, the nucleic acid sample is cooled immediately after heating.

In an aspect, prior to denaturing the nucleic acid sample, the nucleic acid sample is extracted from a viral vector.

In an aspect, the polymer matrix is selected from the group consisting of crosslinked polymer, linear polymers, slightly branched polymers, linear polyacrylamide, polyethylene oxide, polyethylene glycol, dextran, and polyvinylpyrrolidone. In another aspect, the polymer matrix comprises a fluorescent dye. In a further aspect, the fluorescent dye is selected from the group consisting of a cyanine-based dye, SYBR Green II, SYBR gold, SYBR Green I, LIFluor EnhanceCE, and Gel Green. In yet another aspect, the polymer matrix comprises acetic acid or 1,2,5-Thiadiazole.

In an aspect, the nucleic acid sample is diluted with a sample solution, water, or combinations thereof prior to loading on the CE capillary. In another aspect, the sample solution is a sample loading solution. In a further aspect, the sample solution is formamide, dimethyl sulfoxide, guanidine, urea, propylene glycol, and/or sodium salicylate. In another aspect, the water is deionized water or nuclease-free water.

In an aspect, the nucleic acids are separated using capillary zone electrophoresis, capillary gel electrophoresis, capillary isoelectric focusing, micellar electrokinetic capillary chromatography, or capillary electrochromatography.

In an aspect, the detector is a UV detector or fluorescence detector. In another aspect, the detector is a laser-induced fluorescence (LIF) detector, a lamp-based fluorescence detector, or a native fluorescence detector.

One aspect of the disclosure relates to a kit for characterizing nucleic acid purity, wherein the kit comprises a denaturing agent, a CE capillary, a cartridge comprising at least two capillaries, or a capillary electrophoresis chip, a buffer comprising a polymer matrix, and instructions for use.

In an aspect, the denaturing agent is selected from the group consisting of helicase, acetic acid, dimethyl sulfoxide, formamide, formaldehyde, guanidine, urea, propylene glycol, sodium salicylate, 1,2,5-Thiadiazole, and combinations thereof.

In another aspect, the polymer matrix is selected from the group consisting of crosslinked polymer, linear polymers, slightly branched polymers, linear polyacrylamide, polyethylene oxide, polyethylene glycol, dextran, and polyvinylpyrrolidone.

In an aspect, the polymer matrix comprises acetic acid or 1,2,5-Thiadiazole. Other aspects and features of the present disclosure will become apparent to those ordinarily skilled in the art upon review of the following description of specific aspects of the disclosure in conjunction with the accompanying figures.

BRIEF DESCRIPTION OF THE DRAWINGS

Aspects of the present disclosure will now be described, by way of example only, with reference to the attached Figures.

FIG. 13 shows the time program settings for a capillary-conditioning method using the buffer tray setup illustrated in FIG. 10 according to an aspect of the disclosure.

FIG. 14 shows the time program settings for a gel-filling method using the buffer tray setup illustrated in FIG. 10 according to an aspect of the disclosure.

FIG. 15 shows the time program setting for a separation method using the buffer tray setup illustrated in FIG. 10 according to an aspect of the disclosure.

FIG. 17A is from size 122 nt to 169 nt. FIG. 17B is from size 179 nt to 219 nt.

FIG. 18A is from size 122 nt to 169 nt. FIG. 18B is from size 179 nt to 219 nt.

DETAILED DESCRIPTION

Figure 1:
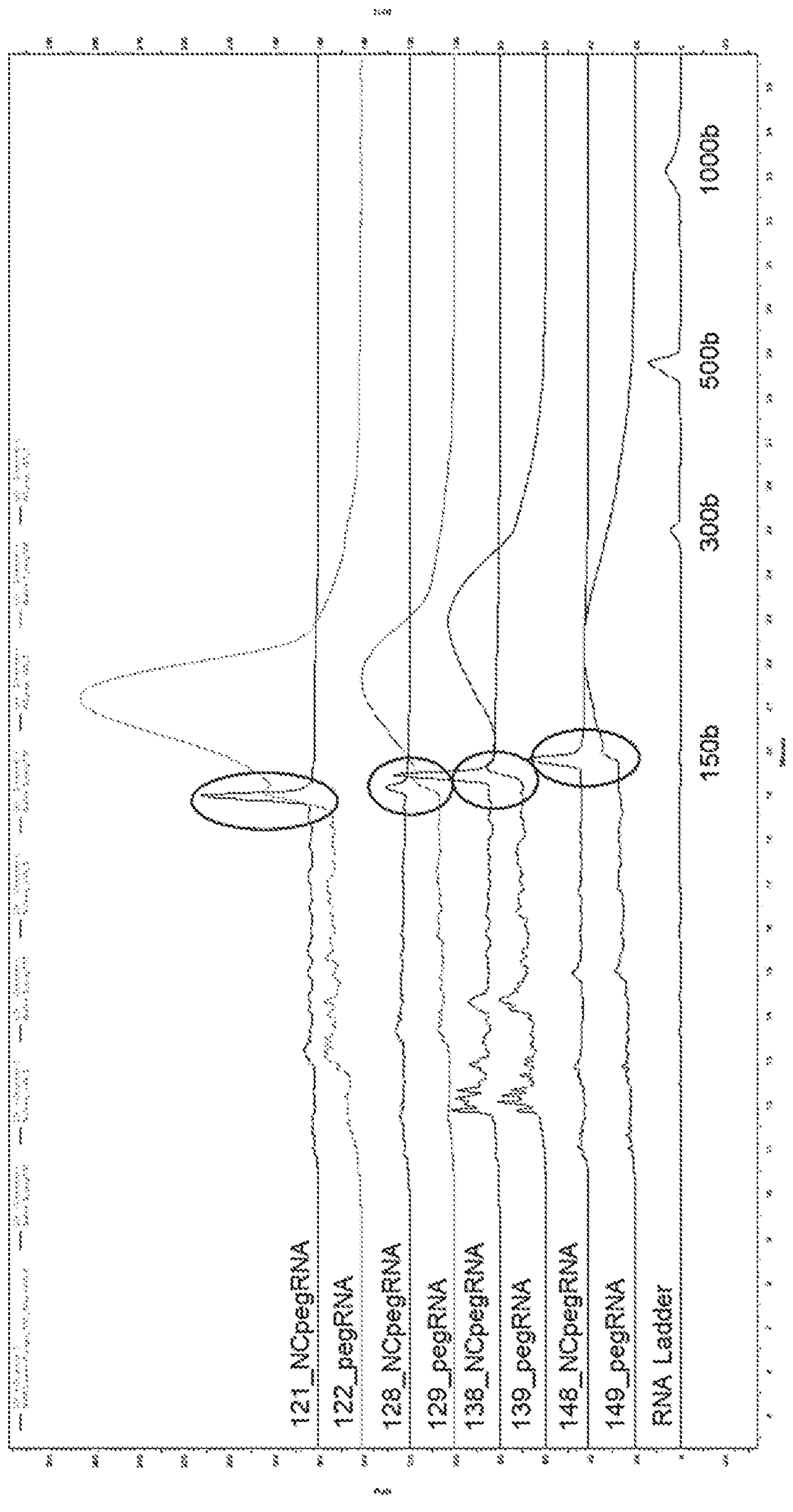
FIG. 1 illustrates a comparison of complementary prime editing guide RNA (pegRNA) and non-complementary prime editing guide RNA (NC pegRNA).

Unless otherwise defined, all technical and scientific terms used herein have the same meaning as commonly understood by one of ordinary skill in the art to which the methods described herein belong.

The singular form "a", "an" and "the" include plural referents unless the context clearly dictates otherwise. These articles refer to one or to more than one (i.e., to at least one). The term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

The term "about" as used in connection with a numerical value throughout the specification and the claims denotes an interval of accuracy, familiar and acceptable to a person skilled in the art. In general, such interval of accuracy is +/−10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

The term "exemplary" means serving as a non-limiting example, instance, or illustration. As utilized herein, the terms "e.g.," and "for example" set off lists of one or more non-limiting aspects, examples, instances, or illustrations.

Aspects of this disclosure include methods for characterizing nucleic acid purity by using a capillary electrophoresis platform. In non-limiting examples, the nucleic acids have complementary or partially complementary sequences. As used herein, "complementary sequences" or "complementary nucleic acid(s)" includes single-stranded nucleic acids wherein the sequence or nucleobases bases of the nucleic acid can be aligned to the sequence or nucleobases of another single-stranded nucleic acid. As used herein, "partially complementary sequence" or "partially complementary nucleic acid(s)" includes single-stranded nucleic acids wherein only a portion of the sequence or nucleobases bases of the nucleic acid can be aligned to the sequence or nucleobases of another single-stranded nucleic acid. These nucleic acids include, for example, ribonucleic acid (RNA), single-stranded DNA (ssDNA), microRNA (miRNA), messenger RNA (mRNA), prime editing guide RNA (pegRNA), and/or self-complementary nucleic acids. Self-complementary nucleic acids include single-stranded nucleic acids that may fold back onto themselves, creating double stand like structures, including, but not limited to, hairpin loops, junctions, bulges, or internal loops. The nucleic acids may also be a component in a nucleic acid sample.

FIG. 1 illustrates a comparison of pegRNA and NC peg RNA. As shown in FIG. 1 there are four pairs of pegRNA and an RNA ladder. Each pair includes RNA oligos of a similar size, but one is pegRNA while the other one is NC pegRNA. The purity analysis shows that traditionally used denaturing methods (65° C., formamide for sample preparation, urea in separation buffer) denatures NCpeg RNAs. However, the majority of the pegRNA molecules are not denatured and instead form higher structure isoforms indicated by the big bump after the sharp peak in the electropherogram. As such, different denaturing and/or sample analysis methods are required to entirely disrupt the hydrogen bonds of ssDNA molecules and maintain the denatured status of these molecules during analysis.

Figure 2:
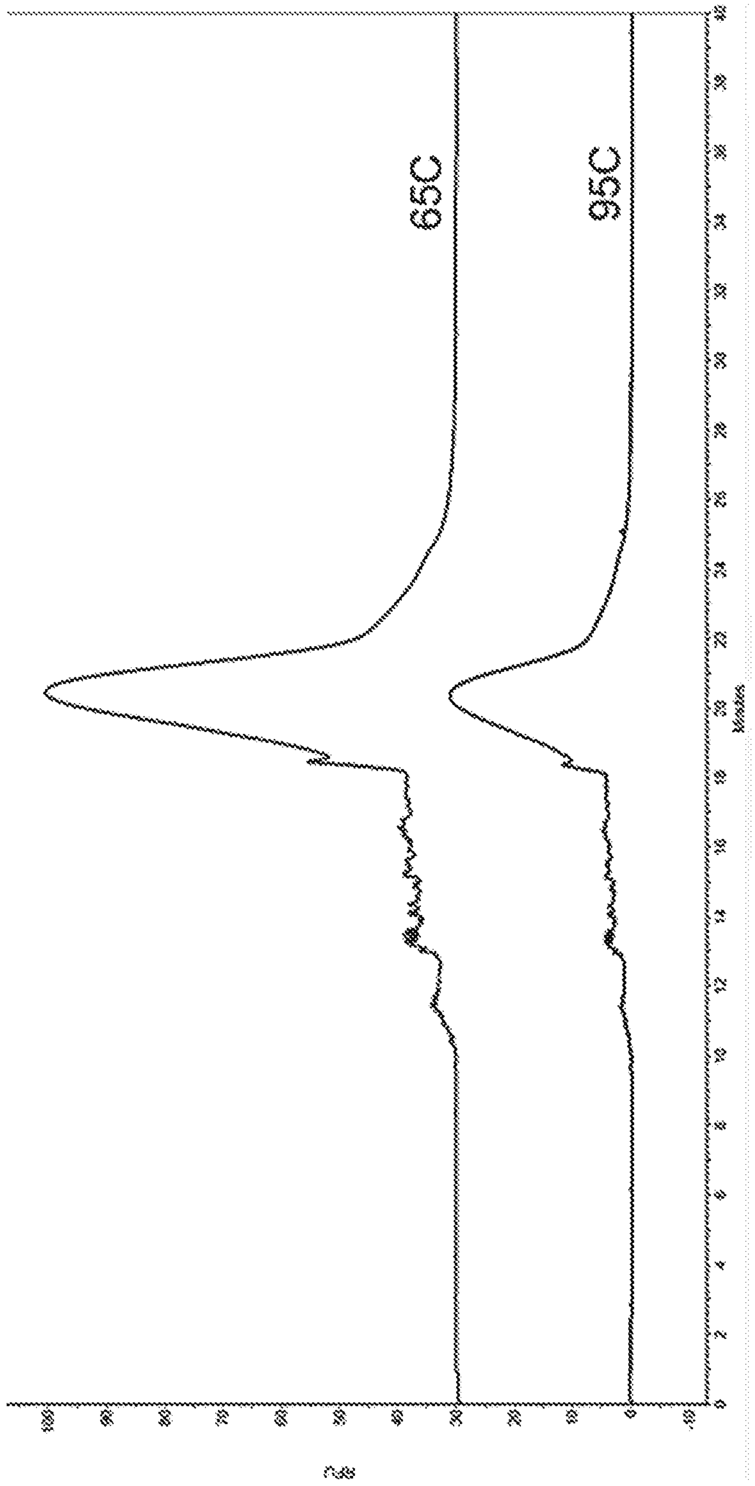
FIG. 2 illustrates heat denaturation of pegRNA during sample preparation.

In an aspect of the disclosure, the nucleic acid purity is characterized, determined, or quantified by denaturing a nucleic acid sample. Heating the nucleic acid sample destabilizes or denatures the nucleic acids. In non-limiting examples, the nucleic acid sample is heated at a temperature between about 60° C. to about 100° C., alternatively at a temperature between about 65° C. to about 95° C., alternatively at a temperature between about 70° C. to about 95° C., alternatively at a temperature between about 75° C. to about 95° C., alternatively at a temperature between about 80° C. to about 95° C., alternatively at a temperature between about 85° C. to about 95° C., alternatively at a temperature between about 90° C. to about 95° C., alternatively at a temperature of about 91° C., alternatively at a temperature of about 92° C., alternatively at a temperature of about 93° C., alternatively at a temperature of about 94° C. FIG. 2 illustrates the heat denaturation of a nucleic acid sample at 65° C. and 95° C. The small sharp peak in front of the bump is a denatured pegRNA molecule, while the bump is a mixture of different high order structures of the pegRNA.

The nucleic acid sample may also be heated for at least about 5 minutes, alternatively at least about 7 minutes, alternatively at least about 9 minutes, alternatively at least about 10 minutes, alternatively at least about 12 minutes, alternatively at least about 15 minutes, alternatively at least about 17 minutes, alternatively at least about 20 minutes, alternatively at least about 22 minutes, alternatively at least about 25 minutes. After heating, in some aspects, the nucleic acid sample is immediately cooled. The nucleic acid sample may be cooled for at least about 1 minute, alternatively at least about 2 minutes, alternatively at least about 3 minutes, alternatively at least about 4 minutes, alternatively at least about 5 minutes, alternatively at least about 10 minutes, alternatively at least about 15 minutes, alternatively at least about 20 minutes, alternatively at least about 30 minutes, alternatively at least about 45 minutes, alternatively at least about 60 minutes.

Figure 3:
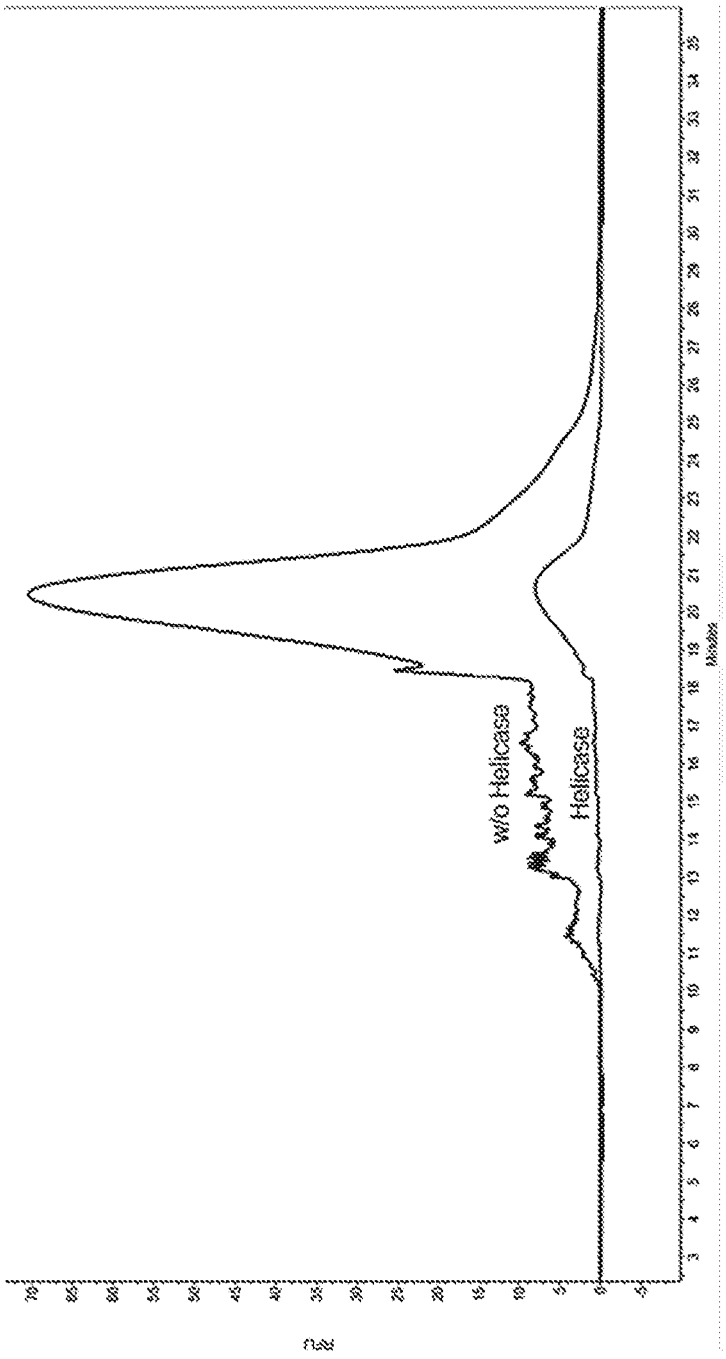
FIG. 3 illustrates enzymatic denaturation of pegRNA during sample preparation.

In addition to heat denaturation, the nucleic acid sample may be further denatured using at least one denaturing agent and/or sonication. Non-limiting examples of denaturing agents include helicase, acetic acid, dimethyl sulfoxide, formamide, formaldehyde, guanidine, urea, propylene glycol, sodium salicylate, 1,2,5-Thiadiazole, and combinations thereof. FIG. 3 illustrates the denaturation of a nucleic acid sample with helicase and heat compared to a nucleic acid sample that was only denatured using heat. The peak intensity decreases when using helicase since the amount of the analytes loaded into the capillary decreases due in part to the electrokinetic injection, which is sensitive to the salt concentration of the sample buffer and the higher salt concentration introduced into the sample solution by the helicase reaction step.

In some aspects, prior to denaturation, the nucleic acid sample is extracted from a viral vector. Extraction may be done using, for example, solid phase extraction, liquid-liquid extraction, a trap-and-elute workflow, filtration, organic solvent extraction, or magnetic based purification.

In an aspect, the denatured nucleic acid sample is loaded onto a capillary electrophoresis (CE) capillary. As used herein, "capillary" refers to a channel, tube, or other structure capable of supporting a volume of separation medium for performing electrophoresis. Capillary geometry can vary and includes structures having circular, rectangular, or square cross-sections, channels, groves, plates, and the like that can be fabricated by technologies known in the art. Capillaries of the present disclosure can be made of materials such as, but not limited to, silica, fused silica, quartz, silicate-based glass such as borosilicate glass, phosphate glass, or alumina-containing glass, and other silica-like materials. In some aspects, the methods can be adapted and used in any generally known electrophoresis platform, such as, for example, electrophoresis devices comprising single or multiple microfluidic channels, etched microfluidic capillaries, as well as slab gel and thin-plate gel electrophoresis.

In an aspect, the nucleic acid sample is diluted prior to being loaded onto the CE capillary. The nucleic acid sample may be diluted with, for example, a sample solution, water, or a combination thereof. The sample solution may be a sample loading solution, and in some aspects, the sample solution is formamide, dimethyl sulfoxide, guanidine, urea, propylene glycol, and/or sodium salicylate. The water may be deionized water or nuclease-free water.

The CE capillary may be filled with a buffer comprising a polymer matrix or gel buffer prior to applying a separation voltage and/or loading the nucleic acid. In some aspects, the buffer comprising a polymer matrix or gel buffer is placed into a buffer vial. These buffer vials may be placed into buffer trays. In some aspects, the buffer comprising a polymer matrix or gel buffer may comprise additional components to facilitate the separation of the nucleic acids. Non-limiting examples of a suitable polymer matrix include crosslinked polymer, linear polymers, slightly branched polymers, linear polyacrylamide, polyethylene oxide, polyethylene glycol, dextran, and polyvinylpyrrolidone.

In some aspects, a fluorescent dye is added to the polymer matrix, the buffer, or both the polymer matrix and the buffer. The fluorescent dyes include, but are not limited to cyanine-based dye, such as Cy2, Cy3, Cy3B, Cy3.5, Cy5, Cy5,5, and Cy7, SYBR Green I, SYBR Green II, SYBR Gold, LIFluor EnhanceCE, Gel Green, PicoGreen, Thiazole orange, and Oxazole yellow. In some aspects, the polymer matrix may comprise a denaturing agent, for example, acetic acid or 1,2,5-Thiadiazole.

Figure 7:
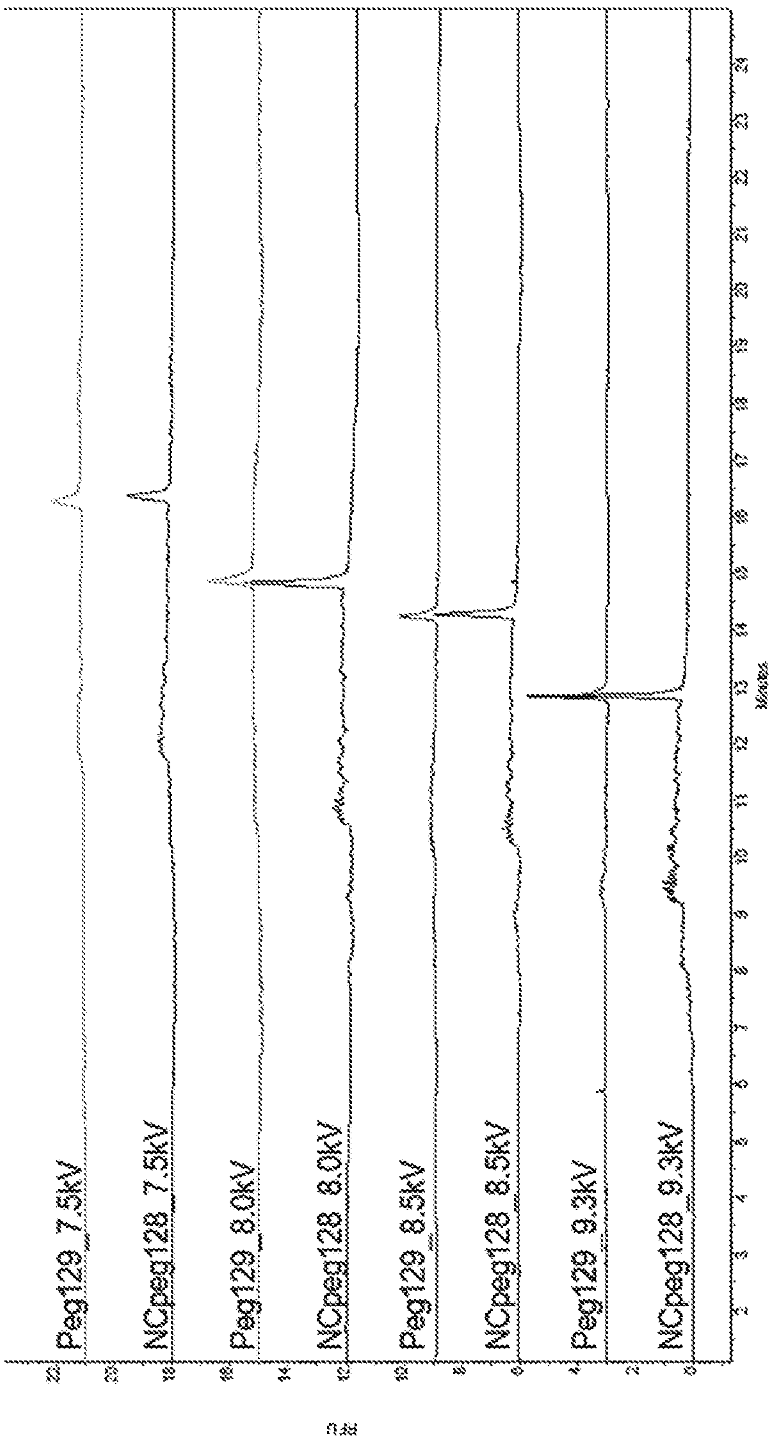
FIG. 7 illustrates the comparison of pegRNA and NC pegRNA separations using increased capillary temperature, and different separation voltages for optimal resolution.

In an aspect, a separation voltage is applied to the CE capillary, and the nucleic acids are moved towards a detector. FIG. 7 illustrates the comparison of separations of pegRNA and NC pegRNA under increased capillary temperatures (50° C.). Different voltages were applied to optimize the resolution of the separation. The voltage may be optimized depending on the size and also the required resolution of the analytes.

The nucleic acids may be separated using capillary zone electrophoresis, capillary gel electrophoresis, capillary isoelectric focusing, micellar electrokinetic capillary chromatography, or capillary electrochromatography. In an aspect, the separation is done using capillary gel electrophoresis (CGE), which separates samples by size and detects nucleic acids using a fluorescent dye that binds to the nucleic acids. In an aspect, the separation is done using capillary zone electrophoresis (CZE), which separates samples by electrophoretic mobility, which is directly proportional to the charge to size ratio on the molecule and inversely proportional to the viscosity of the solvent and hydrodynamic radius of the molecule. CZE can be used to separate nucleic acids of different sizes from the intact lentivirus particle (80 to 100 nanometer). The capillary ID for CZE is usually 50 micrometers.

Figure 4:
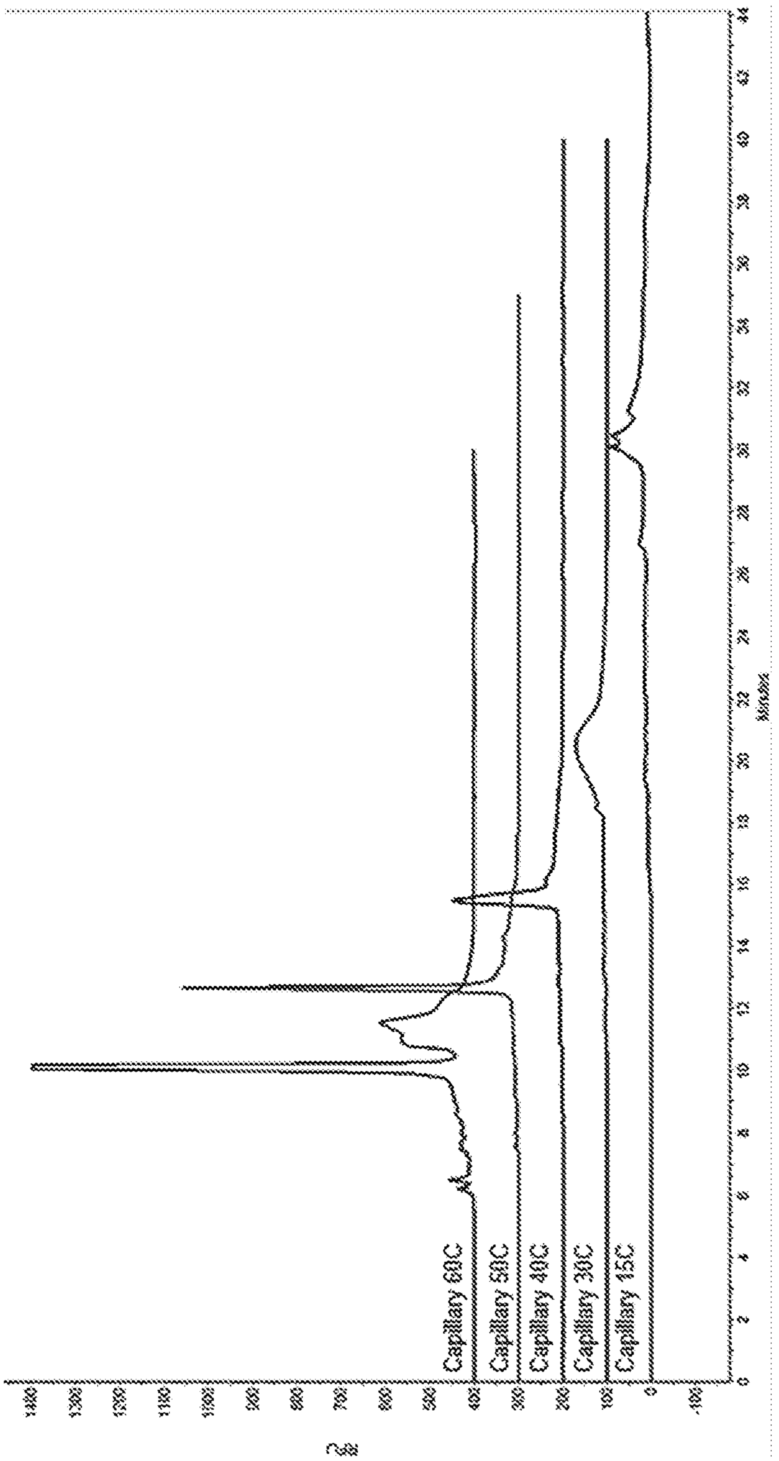
FIG. 4 illustrates the effect of increasing capillary temperatures during the separation of pegRNA denatured using only heat.
Figure 5:
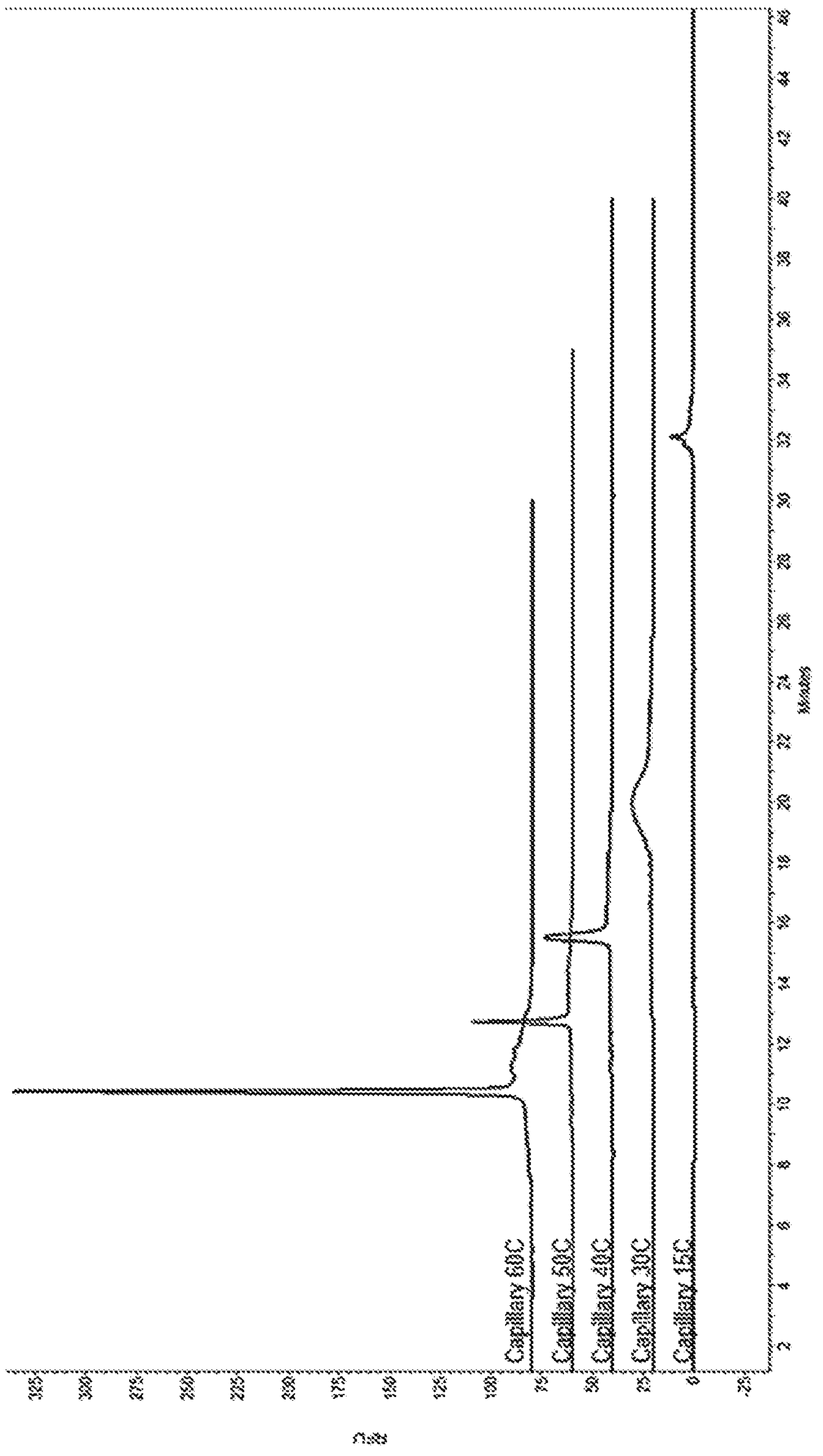
FIG. 5 illustrates the effect of increasing capillary temperatures during the separation of pegRNA denatured using heat and enzymatic treatment.

In an aspect, during the separation of nucleic acids from the nucleic acid sample, the temperature of the CE capillary is increased. In some aspects, the temperature of the CE capillary is set at a temperature that will denature or maintain the denatured status of the nucleic acids during the separation process on the CE instrument. This is particularly helpful for characterizing purity and/or quantifying complementary or partially complementary nucleic acids. In some aspects, the temperature of the CE capillary is increased by least about 5° C., alternatively at least about 10° C., alternatively at least about 15° C., alternatively at least about 20° C., alternatively at least about 25° C., alternatively at least about 30° C., alternatively at least about 35° C., alternatively at least about 40° C., alternatively at least about 45° C. In some aspects, the temperature of the CE capillary during separation is about 15° C., alternatively about 30° C., alternatively about 40° C., alternatively about 50° C., alternatively about 60° C. FIGS. 4 and 5 illustrate the effect of increasing the temperature during the separation of a heat denatured nucleic acid sample (FIG. 4) and a nucleic acid sample denatured using both heat and helicase (FIG. 5). These figures also show the high order structures of pegRNA, which has a high percentage of complementary sequence, are decreasing during the analysis.

Figure 6A:
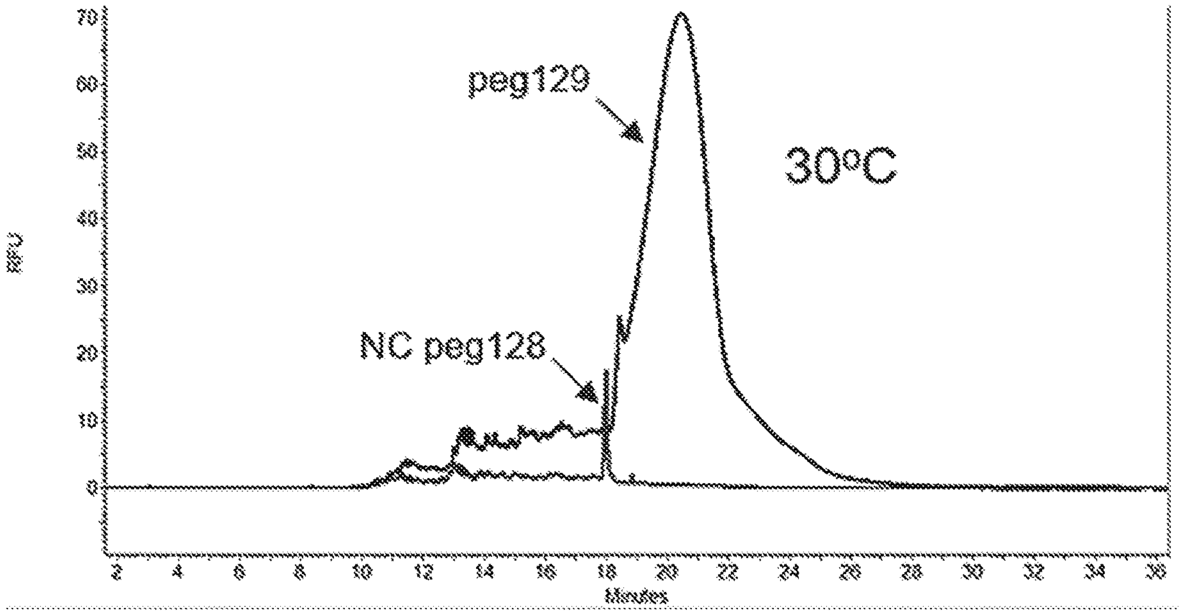
FIGS. 6A and 6B illustrate the effect of increasing capillary temperatures during the separation of pegRNA and NC pegRNA.
Figure 6B:
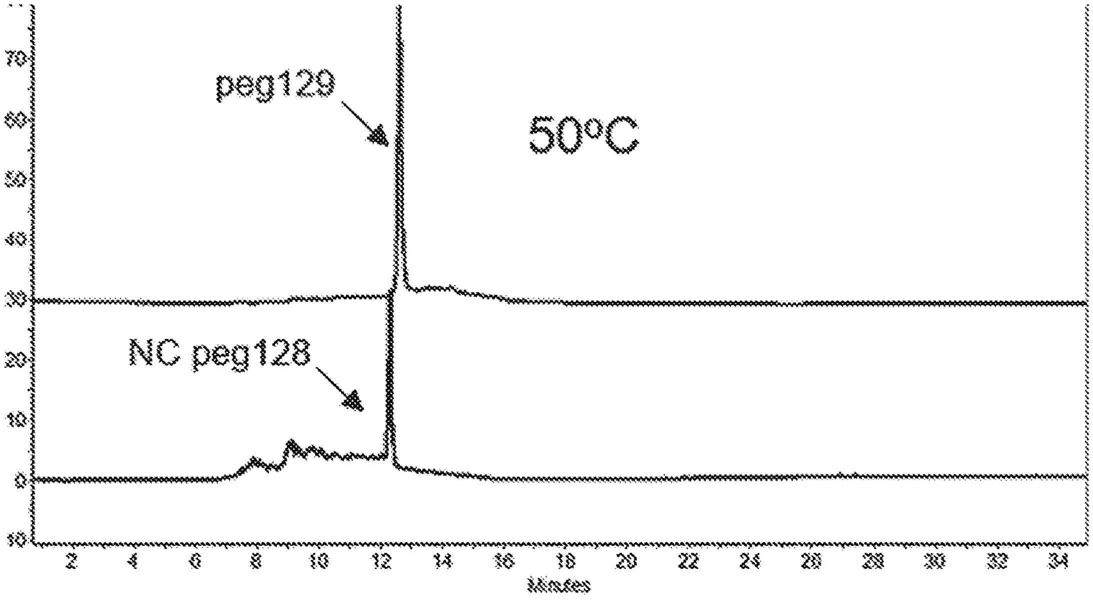

FIGS. 6A and 6B illustrate a comparison of the effects of increasing the temperature to 30° C. (FIG. 6A) and 50° C. (FIG. 6B) on pegRNA with 129 nt and NCpegRNA with 128 nt when separated using capillary gel electrophoresis. The NC pegRNA 128 is used as a control and has a similar length the pegRNA 129. At a 30° C. capillary temperature (FIG. 6A), the pegRNA 129 is not as well denatured as the pegRNA 129 at a capillary temperature of 50° C. (i.e., the big bump after the sharp peak is gone). In this example, when the capillary temperature is higher (e.g., 50° C. versus 30° C.), the pegRNA 129 is well denatured a produces a sharp peak with a migration time slighter behind the NC pegRNA 128 peak. This maintained denatured status allows for the purity analysis of pegRNA 129.

The detector can be a UV detector or a fluorescence detector, such as a laser-induced fluorescence (LIF) detector, a lamp-based fluorescence detector, or a native fluorescence detector. The desired quantitation sensitivity will determine the type of detector used. LIF detection offers the benefit of about an increase in sensitivity, yet it also requires additional sample manipulation.

Another aspect of the disclosure includes a kit for characterizing nucleic acid purity, wherein the kit comprises a denaturing agent, a CE capillary, a cartridge comprising at least two capillaries, or a capillary electrophoresis chip, a buffer comprising a polymer matrix, and instructions for use.

EXAMPLES

Example 1: Exemplary Sample Preparation and Analysis Method

Preparation of the Buffer Comprising a Polymer Matrix 135 ml of DDI water was added to dry Tris-Borate buffer and mixed for 20-30 minutes until the boric acid was completely dissolved. 7M dry urea was added to the Tris-Borate buffer while continuing to stir the solution for 2 hours. The Tris-Borate-Urea (TBE) buffer was filtered, and 10 mL was added to 1 g of ssDNA 100-R gel and the mixture was swirled gently to help the ssDNA-100R gel dissolve. After the gel was completely dissolved, the ssDNA 100-R gel solution was filtered through a 0.45μ disposable syringe filter. If using the LIF detection, SYBR Green II dye was added to the ssDNA 100-R gel solution at a 1:25,000 dilution ratio freshly before the pegRNA sample was run.

Preparation of pegRNA Samples

A 5 nmol pegRNA 129 pellet was reconstituted with 200 μL of nuclease-free (NF) water. 20 μL of the reconstituted pegRNA 129 was diluted in 980 μL of NF water (concentration 0.5 nmol/mL). 10 μL of diluted pegRNA was mixed with 10 μL of formamide and heated at 65° C. for 10 min. The pegRNA sample was then cooled on ice and loaded onto the instrument for further analysis.

Instrument and Software

A PA 800 Plus system equipped with a solid-state laser, LIF detector and UV detector was from SCIEX, Framingham, MA. Data acquisition and analysis were performed using 32 Karat Software (SCIEX, Framingham, MA). A DNA capillary was installed into a capillary cartridge that was installed in the PA 800 Plus system.

Methods

Figure 8:
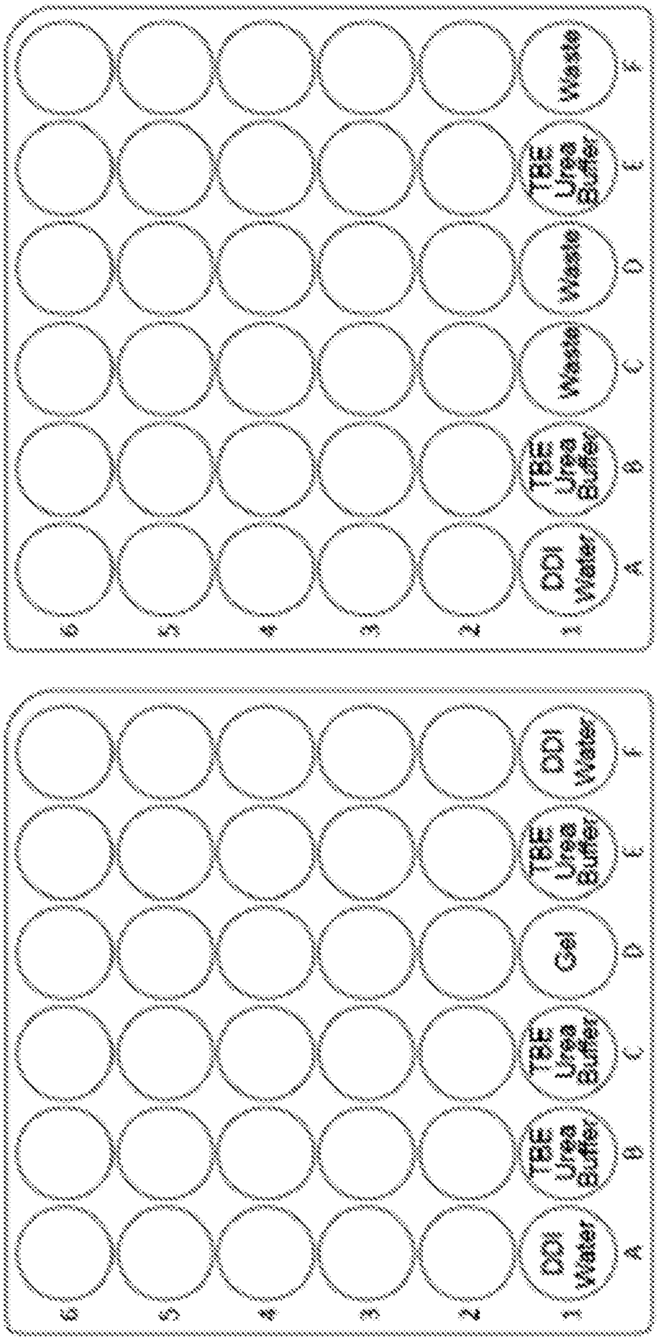
FIG. 8 illustrates a buffer tray inlet (BI), left and a buffer tray outlet (BO), right.
Figure 9:
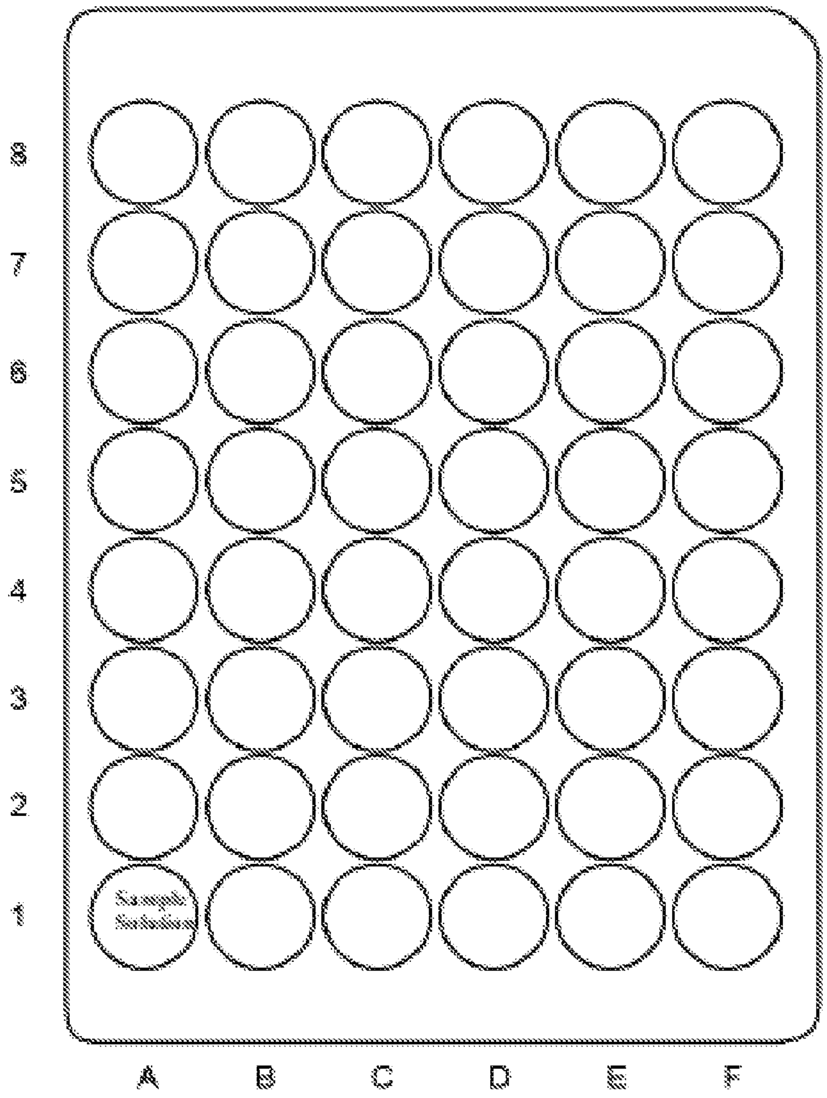
FIG. 9 illustrates a sample tray inlet.

A buffer tray inlet and buffer tray outlet (FIG. 8) were prepared containing DDI water, TBE, and ssDNA 100-R Gel solution. The waste vial contained DDI water. The pegRNA sample was loaded into a sample tray inlet (FIG. 9). The capillary was conditioned using a DDI water rinse, a TBE rinse, and ssDNA 100-gel solution rinse prior to filling the capillary with the ssDNA 100-R gel solution.

The pegRNA was electrokinetically injected onto the capillary, and a 9.3 kV voltage was applied to separate the pegRNA sample. During the separation, the capillary temperature was increased to 50° C. to maintain the denaturation of the pegRNA sample during the separation.

Example 2: Purity Analysis Methods for Synthetic Prime Editing Guide RNAs

The buffer and pegRNA samples were prepared as described in Example 1.

Cartridge Assembly

A DNA capillary (PN 477477) from SCIEX was installed according to the instructions in the ssDNA 100-R kit application guide.4 The total capillary length was 30.2 cm, with 20 cm as the length from the detection window. A 100×200 μm aperture was used for better resolution when using a UV detector. Since the inner wall of the DNA capillary is coated, the cartridge assembly should be carried out promptly. Excessive exposure to air may damage the inner coating and cause clogging. The capillary ends must be immersed in liquid (water or buffer) as soon as the cartridge assembly is complete to prevent the coating from drying out.

Preparation of Buffer Trays and Sample Trays

Figure 10A:
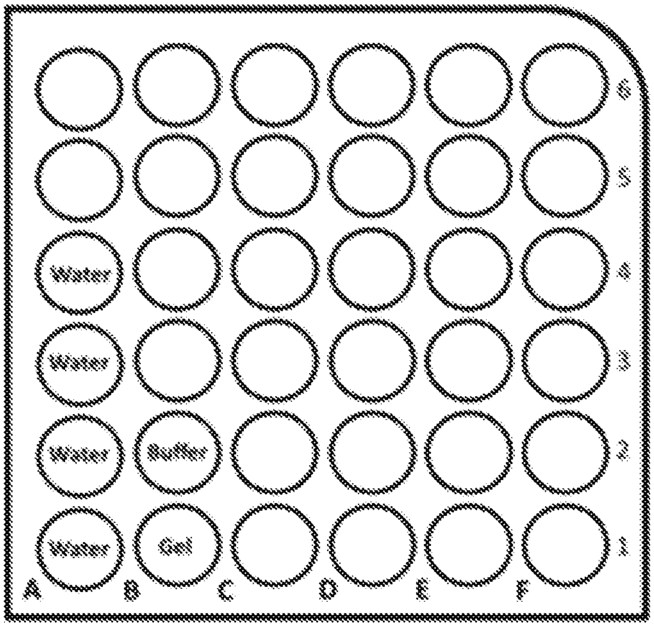
FIGS. 10A and 10B illustrate a schematic setup for inlet (FIG. 10A) and outlet (FIG. 10B) buffer trays.
Figure 10B:
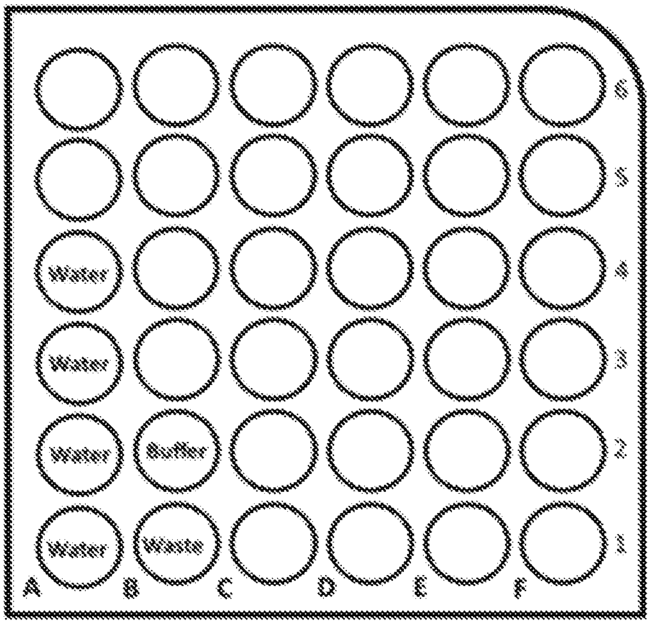

Vial positions for buffer trays are indicated in FIG. 10. Each water vial was filled with 1.5 mL double deionized (DDI) water. The waste vial was filled with 0.8-1.0 mL DDI water. The gel vial was filled with 1.3 mL ssDNA 100-R gel buffer. The gel vial was capped and sonicated to remove the air bubbles before being loaded onto the PA 800 Plus system for analysis. Specifically, the gel vial was sonicated five times for 30 seconds each time, allowing the air bubbles to rise to the surface after each 30-second interval. The buffer vials were filled with 1.5 mL Tris-Borate-Urea buffer.

Instrument Setup

Figure 11:
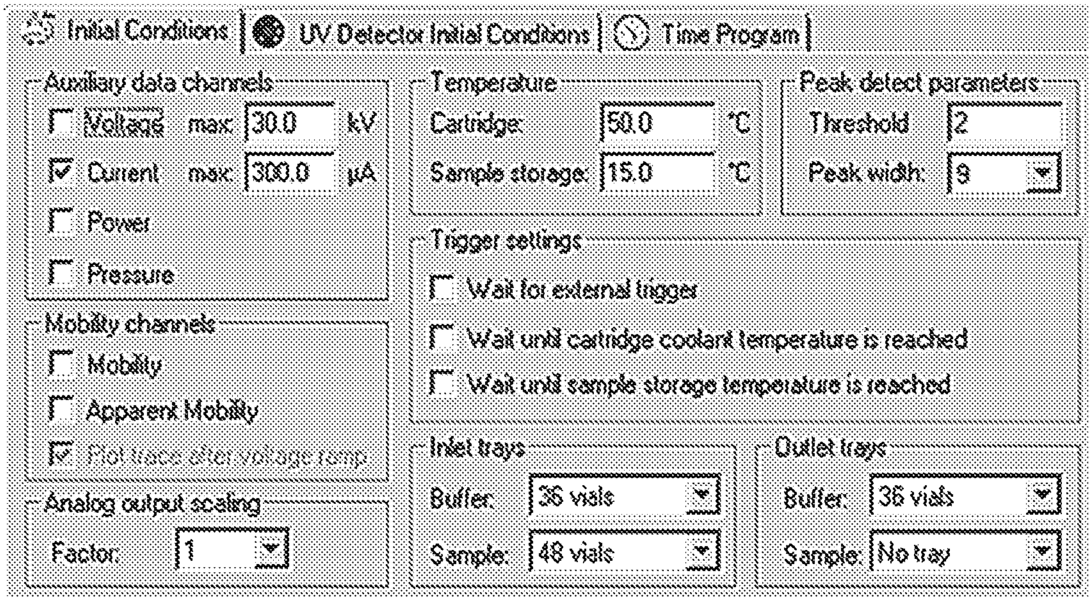
FIG. 11 shows the settings for an initial conditions tab according to an aspect of the disclosure.
Figure 12:
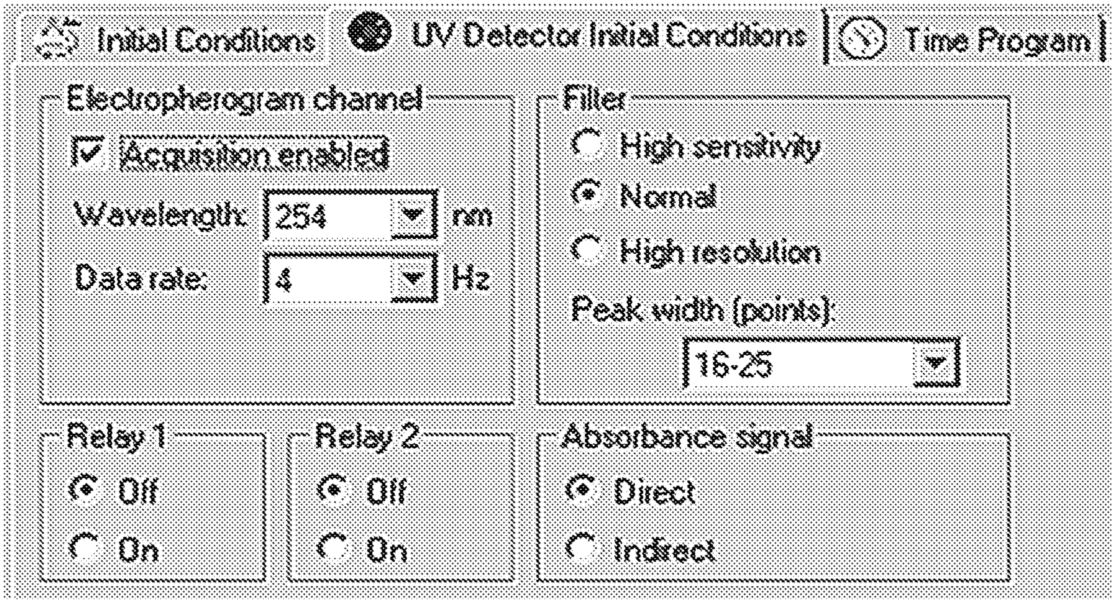
FIG. 12 shows the settings for UV detector initial conditions tab according to an aspect of the disclosure.

The Initial Conditions and UV Detector Initial Conditions were set up as indicated in FIG. 11 and FIG. 12, respectively.

The same setup was used for all three methods: the new capillary-conditioning method, the gel-filling method and the separation method.

Gel Filling and Separation

The Time Program settings for the new capillary-conditioning method are shown in FIG. 13. FIG. 14 and FIG. 15 show the Time Program settings for the gel-filling and separation methods, respectively.

Sample Preparation

Figure 16:
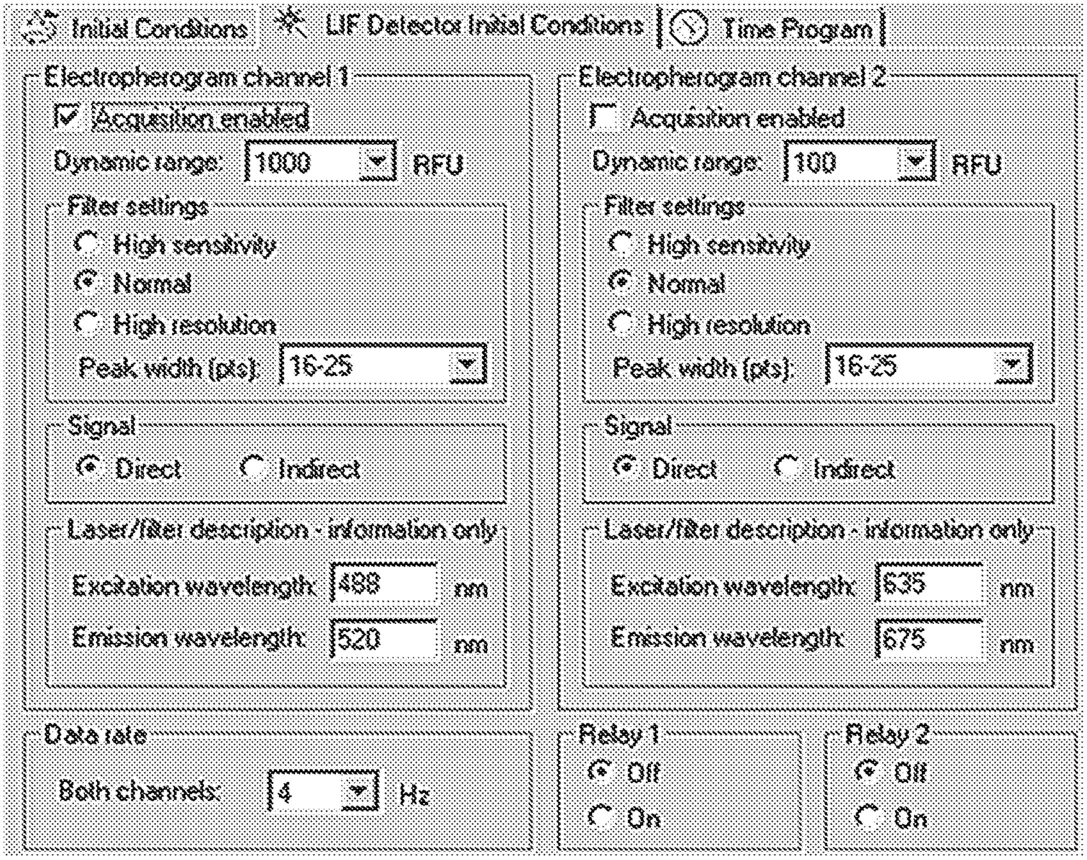
FIG. 16 shows settings a LIF Detector Initial Conditions tab according to an aspect of the disclosure.
Figure 17A:
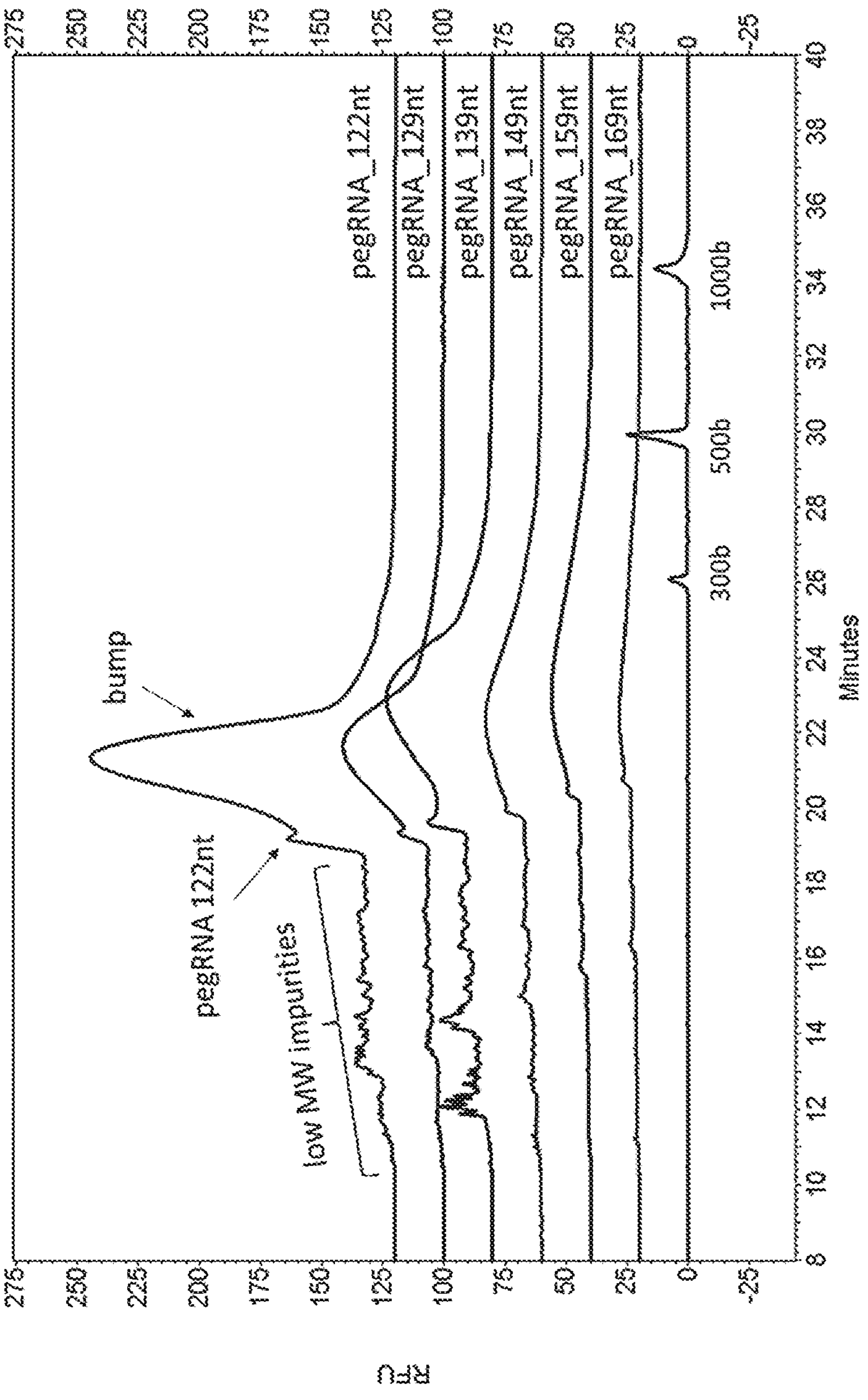
FIGS. 17A and 17B show an analysis of pegRNAs using a method according to an aspect of the disclosure, but without optimization of the denaturation of the pegRNAs during separation.
Figure 17B:
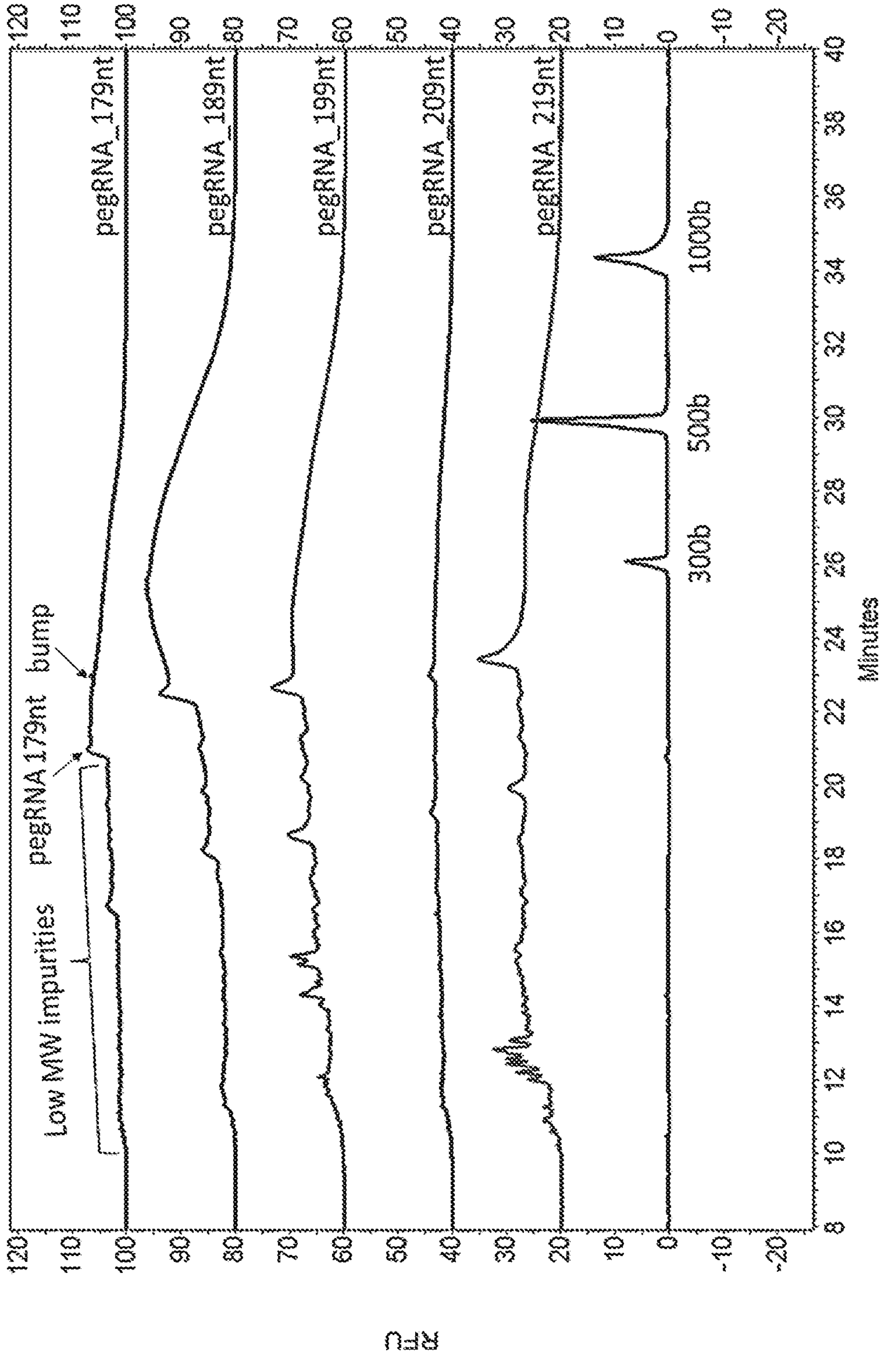

The RNA oligonucleotides were diluted with nuclease-free water to about 0.5-1 μM and then loaded into the sample insert tube (a minimum sample volume of 40 μL) or the nanoVial (a minimum sample volume of 5 μL). Sample vials were loaded onto the sample inlet tray for analysis. To analyze oligonucleotides with ultra-low concentration, the SYBR Green II RNA gel stain and the LIF detector were used to achieve high sensitivity. First, the Tris-Borate-Urea buffer was mixed with the SYBR Green II RNA gel stain at a ratio of 25,000 to 1. The settings for the LIF Detector Initial Conditions are shown in FIG. 16.

Purity Analysis of pegRNAs pegRNA oligonucleotides with lengths of 122 nt, 129 nt, 139 nt, 149 nt, 159 nt, 169 nt, 179 nt, 189 nt, 199 nt, 209 nt and 219 nt, together with an RNA ladder (50-1,000 bases), were analyzed using the described methods with non-optimized denaturing condition (capillary temperature at 30° C.). All the pegRNA samples show a sharp peak followed by a big bump.

To investigate the root cause of the abnormal peak shape of pegRNAs, four non-complementary RNAs (NC RNAs) at various lengths (121 nt, 128 nt, 138 nt and 148 nt) were designed with the minimal possibility of forming secondary structures and analyzed together with pegRNAs of similar lengths (122 nt, 129 nt, 139 nt and 149 nt) using the described methods with non-optimized denaturing condition (capillary temperature at 30° C.). As shown in FIG. 1, all NC RNAs showed a singular peak without the big bump, indicating that the abnormal peak shape of pegRNAs was probably due to their secondary structures.

Figure 18A:
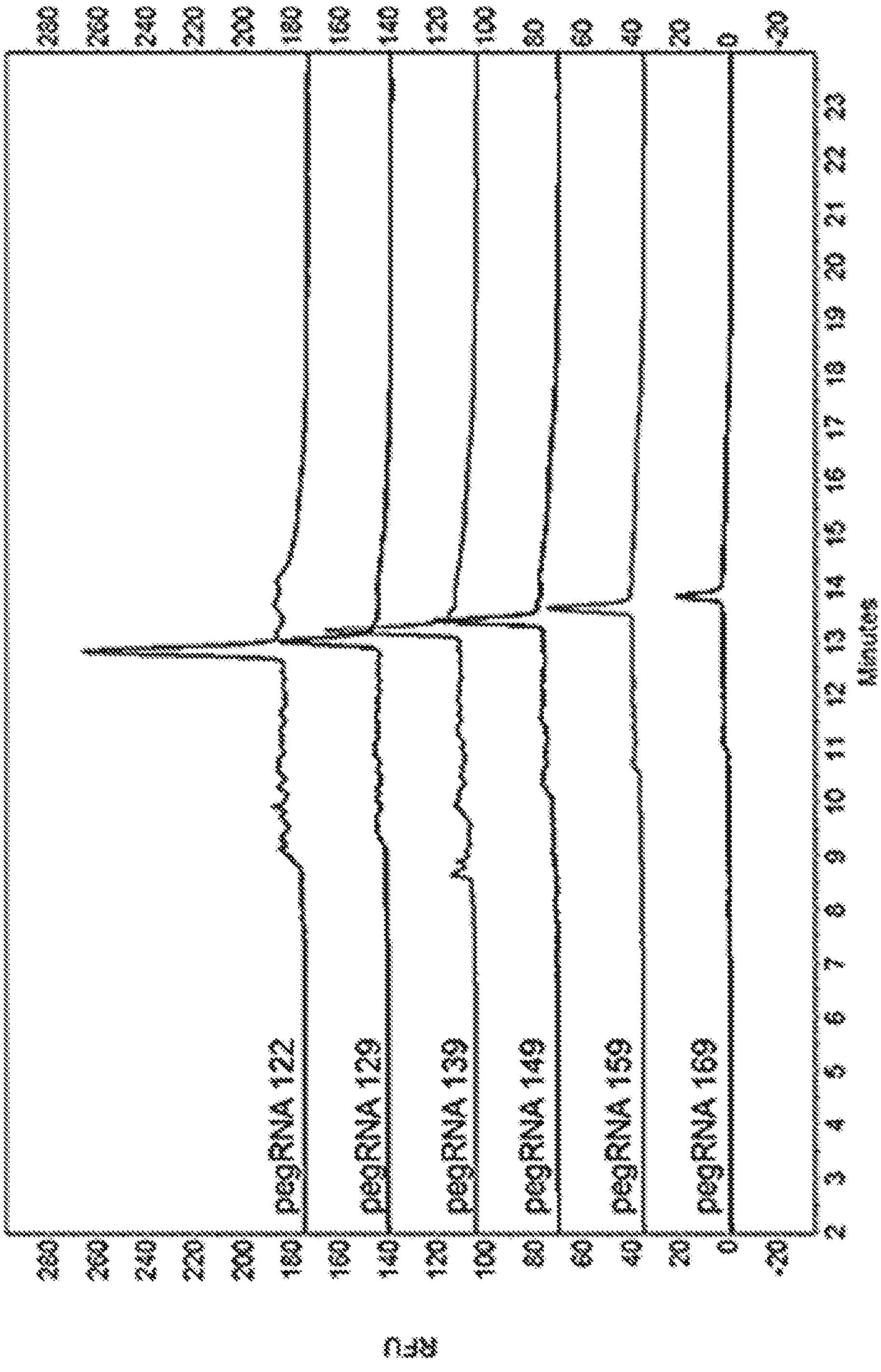
FIGS. 18A and 18B show pegRNA analysis using the optimized denaturing strategies and the optimized gel matrix for long oligonucleotides.
Figure 18B:
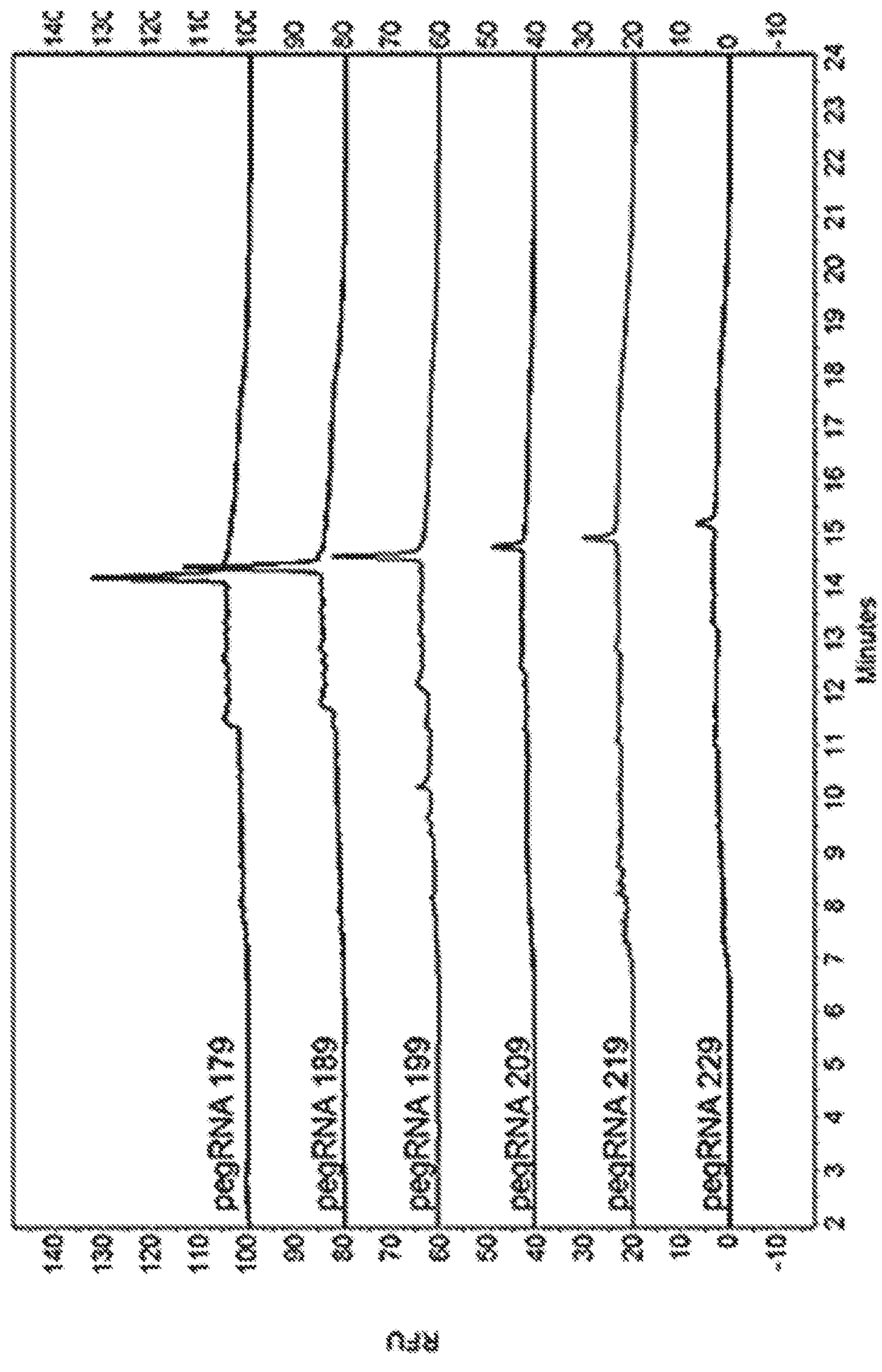

The pegRNA samples were prepared by mixing with formamide and heating at 65° C. for 10 minutes. Then, the capillary temperature was increased to 50° C. to maintain the pegRNA sample under a denatured state during the separation. As shown in FIGS. 18A and 18B, a single, sharp peak has been obtained for all the tested pegRNA samples with the increased separation temperature.

Figure 19:
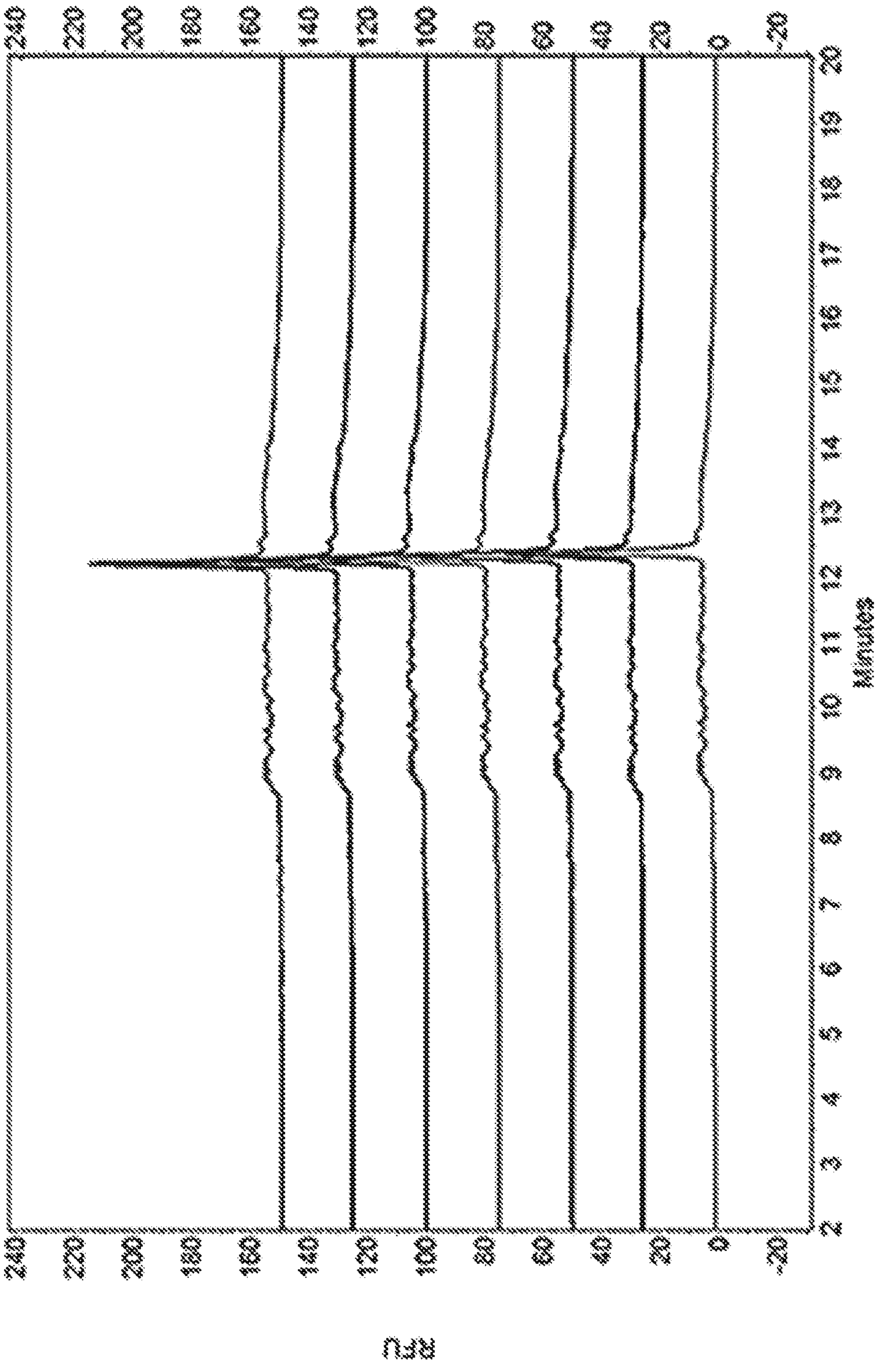
FIG. 19 shows repeatability of pegRNA analysis using the optimized denaturing strategies and the optimized gel matrix for long oligonucleotides.

A repeatability study of a representative pegRNA with a size of 129 nt was performed by seven consecutive injections. As shown in FIG. 19, peak profile, migration time and signal level were very consistent between the seven injections. The RSD % of migration time (MT) and the corrected peak area % (CPA %) of full-length product (FLP) were 1.61% and 2.45%, respectively. The liquid cooling feature of the capillary temperature on the system enables stable and accurate temperature control during the separation, therefore providing a robust platform for maintaining the denatured status of pegRNA oligonucleotides. After trialing various denaturation methods, the ability to resolve pegRNA sequences into a single, sharp peak has been achieved and % FLP can be determined. Accurate and repeatable purity analysis of pegRNAs was achieved after establishing the optimized sample treatment and capillary electrophoresis conditions.

While the present disclosure has been described with reference to certain aspects, it will be understood by those skilled in the art that various changes may be made and equivalents may be substituted without departing from the scope of the present disclosure or appended claims. In addition, many modifications may be made to adapt a particular situation or material to the teachings of the present disclosure without departing from its scope. Therefore, it is intended that the present disclosure not be limited to the particular aspects disclosed but that the present disclosure will include all aspects falling within the scope of the appended claims.

All patents, patent applications, publications, and descriptions mentioned above are herein incorporated by reference in their entirety.

What is claimed is:

1. A method for characterizing nucleic acid purity comprising:

denaturing a nucleic acid sample comprising complementary prime editing guide RNA (pegRNA), wherein the nucleic acid sample is denatured using heat;

loading the nucleic acid sample onto a capillary electrophoresis (CE) capillary, wherein the CE capillary is filled with a buffer comprising a polymer matrix;

applying a separation voltage to the CE capillary, wherein during the separation of the nucleic acids, the temperature of the CE capillary is increased to at least 40° C.;

and detecting nucleic acids separated from the nucleic acid sample with a detector.

2. The method of claim 1, wherein the nucleic acid sample is denatured using at least one denaturing agent.

3. The method of claim 2, wherein the denaturing agent is selected from the group consisting of helicase, acetic acid, dimethyl sulfoxide, formamide, formaldehyde, guanidine, urea, propylene glycol, sodium salicylate, 1,2,5-Thiadiazole, and combinations thereof.

4. The method of claim 1, wherein the nucleic acid sample is denatured using sonication.

5. The method of claim 1, wherein the nucleic acid sample is heat denatured at a temperature of between about 60° C. and about 95° C.

6. The method of claim 5, wherein the nucleic acid sample is cooled immediately after heating.

7. The method of claim 1, wherein the nucleic acid sample is heat denatured for at least about 5 minutes.

8. The method of claim 1, wherein prior to denaturing the nucleic acid sample, the nucleic acid sample is extracted from a viral vector.

9. The method of claim 1, wherein the polymer matrix is selected from the group consisting of crosslinked polymer, linear polymers, slightly branched polymers, linear polyacrylamide, polyethylene oxide, polyethylene glycol, dextran, and polyvinylpyrrolidone.

10. The method of claim 1, wherein the polymer matrix comprises a fluorescent dye.

11. The method of claim 10 wherein the fluorescent dye is selected from the group consisting of a cyanine-based dye, SYBR Green II, SYBR gold, SYBR Green I, LIFluor EnhanceCE, and Gel Green.

12. The method of claim 1, wherein the polymer matrix comprises acetic acid or 1,2,5-Thiadiazole.

13. The method of claim 1, wherein the nucleic acid sample is diluted with a sample solution, water, or combinations thereof prior to loading on the CE capillary.

14. The method of claim 13, wherein the sample solution is a sample loading solution.

15. The method of claim 13, wherein the sample solution is formamide, dimethyl sulfoxide, guanidine, urea, propylene glycol, and/or sodium salicylate.

16. The method of claim 13, wherein the water is deionized water or nuclease-free water.

17. The method of claim 1, wherein the detector is a UV detector or fluorescence detector.

18. The method of claim 17, wherein the detector is a laser-induced fluorescence (LIF) detector, a lamp-based fluorescence detector, or a native fluorescence detector.

* * * * *